United States Patent
Long et al.

(10) Patent No.: US 9,789,010 B2
(45) Date of Patent: Oct. 17, 2017

(54) ABSORBENT ARTICLE HAVING A TEAR AWAY SECTION

(71) Applicant: Kimberly-Clark Worldwide, Inc., Neenah, WI (US)

(72) Inventors: Andrew Long, Appleton, WI (US); Julie Paveletzke, Neenah, WI (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 144 days.

(21) Appl. No.: 14/231,428

(22) Filed: Mar. 31, 2014

(65) Prior Publication Data

US 2015/0272788 A1    Oct. 1, 2015

(51) Int. Cl.
| | |
|---|---|
| A61F 13/15 | (2006.01) |
| A61F 13/496 | (2006.01) |
| A61F 13/84 | (2006.01) |
| A61F 13/49 | (2006.01) |

(52) U.S. Cl.
CPC ............ *A61F 13/496* (2013.01); *A61F 13/84* (2013.01); *A61F 2013/49098* (2013.01)

(58) Field of Classification Search
CPC .......... A61F 13/01004; A61F 13/49098; A61F 13/493; A61F 13/565; A61F 13/5655; A61F 13/8402
See application file for complete search history.

(56) References Cited

U.S. PATENT DOCUMENTS

| | | |
|---|---|---|
| 507,485 A | 10/1893 | Carr et al. |
| 4,100,324 A | 7/1978 | Anderson et al. |
| 4,610,680 A | 9/1986 | LaFleur |
| 4,619,649 A * | 10/1986 | Roberts .................. A61F 5/4401 604/385.29 |
| 4,663,220 A | 5/1987 | Wisneski et al. |
| 4,747,846 A | 5/1988 | Boland et al. |
| 4,909,804 A | 3/1990 | Douglas, Sr. |
| 4,940,464 A | 7/1990 | Van Gompel et al. |

(Continued)

FOREIGN PATENT DOCUMENTS

| | | |
|---|---|---|
| EP | 0217032 | 4/1987 |
| WO | 8907897 | 9/1989 |
| WO | 0188245 | 11/2001 |

OTHER PUBLICATIONS

International Search Report and Written Opinion for International Application No. PCT/IB2015/051658, dated May 21, 2015, 15 pages.

*Primary Examiner* — Bradley Philips
(74) *Attorney, Agent, or Firm* — Armstrong Teasdale LLP

(57) ABSTRACT

A disposable absorbent article includes a bodyside liner, an outer cover, an absorbent body disposed between the liner and the outer cover, a front waist region, a back waist region, a crotch region extending between and interconnecting the front and back waist regions, and a tear away section configured to be torn from the absorbent article when at least a threshold force is applied to the tear away section. The front and back waist regions are attached to each other by side panels at least partially defining leg openings and a waist opening of the absorbent article. The tear away section extends from the waist opening to a respective leg opening and is defined by at least one line of weakness. The tear away section has a tear strength greater than the threshold force.

16 Claims, 8 Drawing Sheets

(56) References Cited

U.S. PATENT DOCUMENTS

| | | |
|---|---|---|
| 5,046,272 A | 9/1991 | Vogt et al. |
| 5,104,116 A | 4/1992 | Pohjola |
| 5,224,405 A | 7/1993 | Pohjola |
| 5,226,992 A | 7/1993 | Morman |
| 5,284,703 A | 2/1994 | Everhart et al. |
| 5,350,624 A | 9/1994 | Georger et al. |
| 5,385,775 A | 1/1995 | Wright |
| 5,486,166 A | 1/1996 | Bishop et al. |
| 5,490,846 A | 2/1996 | Ellis et al. |
| 5,624,420 A | 4/1997 | Bridges et al. |
| 5,820,973 A | 10/1998 | Dodge, II et al. |
| 6,057,024 A | 5/2000 | Mleziva et al. |
| 6,302,871 B1 | 10/2001 | Nakao et al. |
| 6,525,238 B2 * | 2/2003 | Corrales ............... A61F 15/00 600/499 |
| 6,916,750 B2 | 7/2005 | Thomas et al. |
| 6,969,441 B2 | 11/2005 | Welch et al. |
| 7,744,577 B2 | 6/2010 | Otsubo et al. |
| 7,803,244 B2 | 9/2010 | Siqueira et al. |
| 8,066,687 B2 * | 11/2011 | Ashton ............ A61F 13/15203 604/386 |
| 8,361,913 B2 | 1/2013 | Siqueira et al. |
| 2002/0111596 A1 | 8/2002 | Fletcher et al. |
| 2004/0186451 A1 * | 9/2004 | Bishop ................ A61F 13/493 604/385.11 |
| 2006/0167434 A1 | 7/2006 | Ashton et al. |
| 2007/0233033 A1 | 10/2007 | Ichikawa et al. |
| 2008/0114322 A1 * | 5/2008 | Schmoker ........ A61F 13/15268 604/385.03 |
| 2009/0149827 A1 * | 6/2009 | Mlinar ................ A61F 13/4902 604/385.14 |
| 2011/0313380 A1 | 12/2011 | Ashton et al. |
| 2012/0101468 A1 * | 4/2012 | Sperl .................. A61F 13/4963 604/385.24 |
| 2012/0157953 A1 * | 6/2012 | Ashton ................ A61F 13/496 604/385.16 |
| 2013/0231629 A1 | 9/2013 | Paveletzke et al. |

* cited by examiner

ABSORBENT ARTICLE HAVING A TEAR AWAY SECTION

BACKGROUND

The present disclosure relates generally to absorbent articles intended for personal wear, and more particularly to disposable pull-on absorbent articles having a tear away section for quick and easy removal of the article from the wearer.

Exemplary pull-on absorbent articles include training pants, diaper pants, incontinence products, disposable underwear, medical garments, absorbent swim wear, and the like. Pull-on type absorbent articles are absorbent articles configured to be donned by pulling the article up around the wearer's legs. When soiled, typical pull-on type absorbent articles must be doffed by sliding the pant down around the wearer's legs, which can result in bodily exudates (e.g., urine or fecal matter) spilling or leaking out of the training pant.

Toilet training is a process that includes many training techniques and aids that can be used by parents or other caregivers. One aspect of the total toilet training process is changing from the use of diapers to the use of training pants to help the child understand that he or she should now use the toilet. This process involves teaching a child to remove the training pant before going to the bathroom. When typical pull-on training pants are used as a training aid, the training pant is pulled down around the wearer's legs before the wearer can go to the bathroom. When the child has an urgent need to go to the bathroom, the process of removing typical training pants can be slow, and often ineffective in teaching a child to use the toilet.

Some current training pants include refastenable side seams that enable the training pant to be donned and doffed without pulling the training pant up or down the wearer's legs. Such refastenable side seams facilitate both donning and doffing the training pant, as the training pants do not have be pulled up or down the wearer's legs to don or doff the training pant. However, users of such training pants are often unaware that the side seams are refastenable, and often only utilize the refastenable side seams in removing the training pant from the wearer. Providing such refastenable side seams on training pants requires the use of additional materials (e.g., hook and loop type fasteners), and often makes the manufacturing process more complex, thereby increasing the cost of manufacturing such training pants. As a result, the refastenable side seams of such training pants are a relatively costly feature when used only in removing the training pant from the wearer.

Other current training pants include side seams that can be torn to remove the training pant from the wearer. However, such training pants typically require the use of two hands to tear the side seams. As a result, the side seams of such training pants can only be torn one at a time, thus increasing the overall time needed to remove the training pant.

Accordingly, a need exists for a pull-on absorbent article that can be quickly and easily removed from the wearer.

SUMMARY

In one aspect, a disposable absorbent article generally comprises a bodyside liner, an outer cover, an absorbent body disposed between the liner and the outer cover, a front waist region, a back waist region, a crotch region extending between and interconnecting the front and back waist regions, and a tear away section configured to be torn from the absorbent article when at least a threshold force is applied to the tear away section. The front and back waist regions are attached to each other by side panels at least partially defining leg openings and a waist opening of the absorbent article. The tear away section extends from the waist opening to a respective leg opening and is defined by at least one line of weakness. The tear away section has a tear strength greater than the threshold force.

In another aspect, a disposable absorbent article includes a bodyside liner, an outer cover, an absorbent body disposed between the liner and the outer cover, a front waist region, a back waist region, a crotch region extending between and interconnecting the front and back waist regions, and a tear away section configured to be torn from the absorbent article to facilitate removal of the absorbent article from a wearer. The front and back waist regions are attached to each other by side panels at least partially defining leg openings and a waist opening of the absorbent article. The tear away section extends from the waist opening to a respective leg opening and is defined by at least one line of weakness. The tear away section includes a reinforcing element configured to prevent a tear from propagating through the tear away section.

In yet another aspect, a disposable absorbent article includes a bodyside liner, an outer cover, an absorbent body disposed between the bodyside liner and the outer cover, a front waist region, a back waist region, a crotch region extending between and interconnecting the front and back waist regions, and a tear away section configured to be torn from the absorbent article to facilitate removal of the absorbent article from a wearer. The front and back waist regions are attached to each other by side panels at least partially defining leg openings and a waist opening of the absorbent article. The tear away section extends from the waist opening to a respective leg opening and includes a reinforcing element and a grip tab. The grip tab includes a visual cue for enhancing the noticeability of the grip tab.

Other features of this disclosure will be in part apparent and in part pointed out hereinafter.

BRIEF DESCRIPTION OF THE DRAWINGS

Corresponding reference characters indicate corresponding parts throughout the several views of the drawings.

DETAILED DESCRIPTION OF THE DRAWINGS

Figure 1:
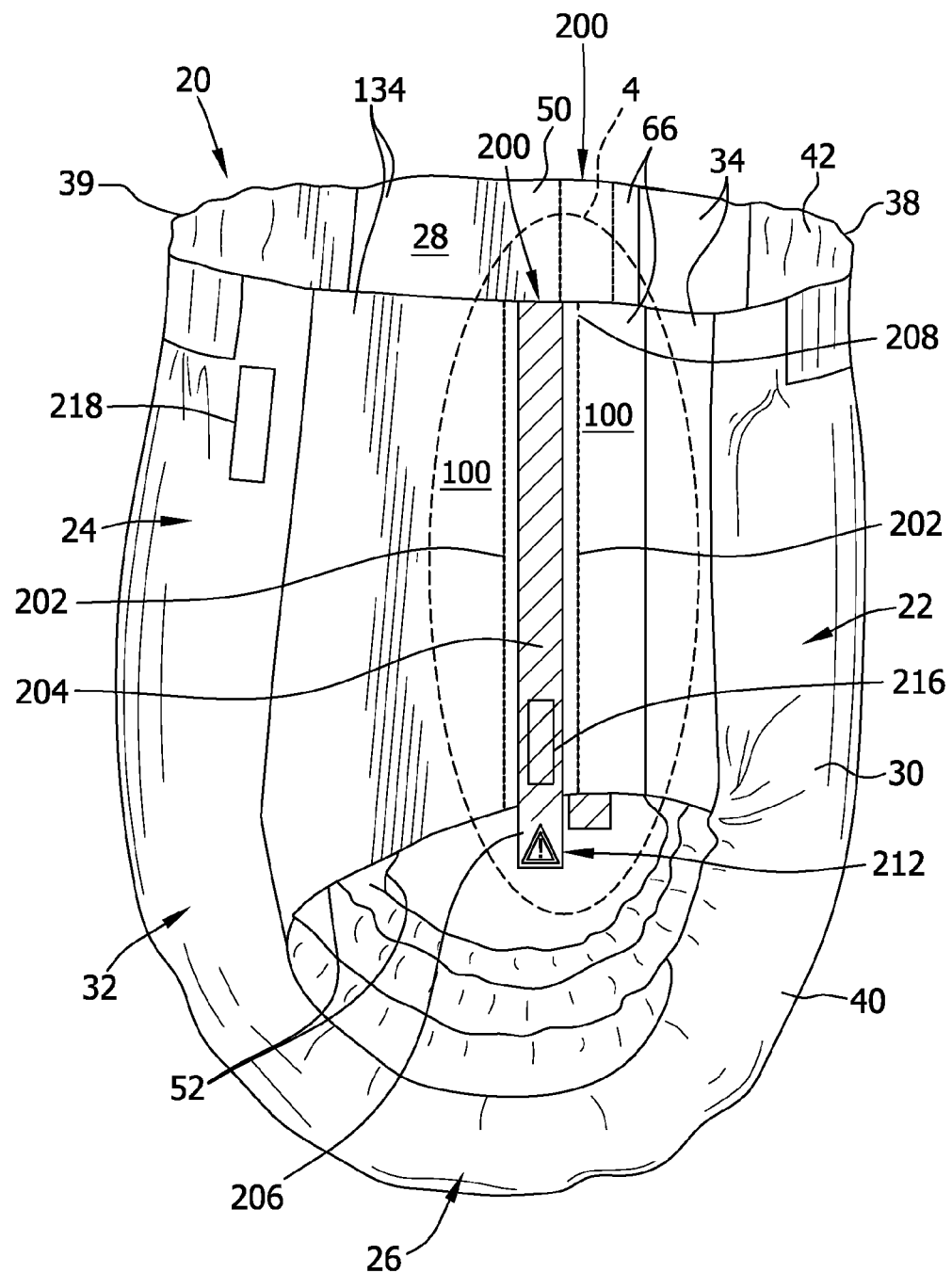
FIG. 1 is a side perspective of one suitable embodiment of an absorbent article shown in the form of a training pant, the training pant having a tear away section.

Referring now to the drawings and in particular to FIG. 1, one suitable embodiment of an absorbent article is illustrated in the form of a child's toilet training pant and is indicated in its entirety by the reference numeral 20. The term absorbent article generally refers to articles that may be placed against or in proximity to a body of a wearer to absorb and/or retain various exudates from the body. The absorbent training pant 20 may or may not be disposable. Disposable refers to articles that are intended to be discarded after a limited period of use instead of being laundered or otherwise conditioned for reuse. It is understood that the embodiments of the present disclosure are suitable for use with various other absorbent articles intended for personal wear, including but not limited to diaper pants, swim diapers, feminine hygiene products (e.g., sanitary napkins), incontinence products, medical garments, surgical pads and bandages, other personal care or health care garments, and the like without departing from the scope of the present disclosure.

The training pant 20 is illustrated in FIG. 1 in a fully assembled (i.e., as assembled during initial manufacture) configuration (broadly referred to herein as a wear configuration of the pant 20). The training pant 20 comprises a front waist region 22, a back waist region 24, a crotch region 26 extending longitudinally between and interconnecting the front and back waist regions along a longitudinal direction of the pant 20, an inner surface 28 configured for contiguous relationship with the wearer, and an outer surface 30 opposite the inner surface. With additional reference to FIGS. 2 and 3, the training pant 20 also has a pair of laterally opposite side edges 36 and a pair of longitudinally opposite waist edges, respectively designated the front waist edge 38 and the back waist edge 39. The front waist region 22 is contiguous with the front waist edge 38, and the back waist region 24 is contiguous with the back waist edge 39.

Figure 2:
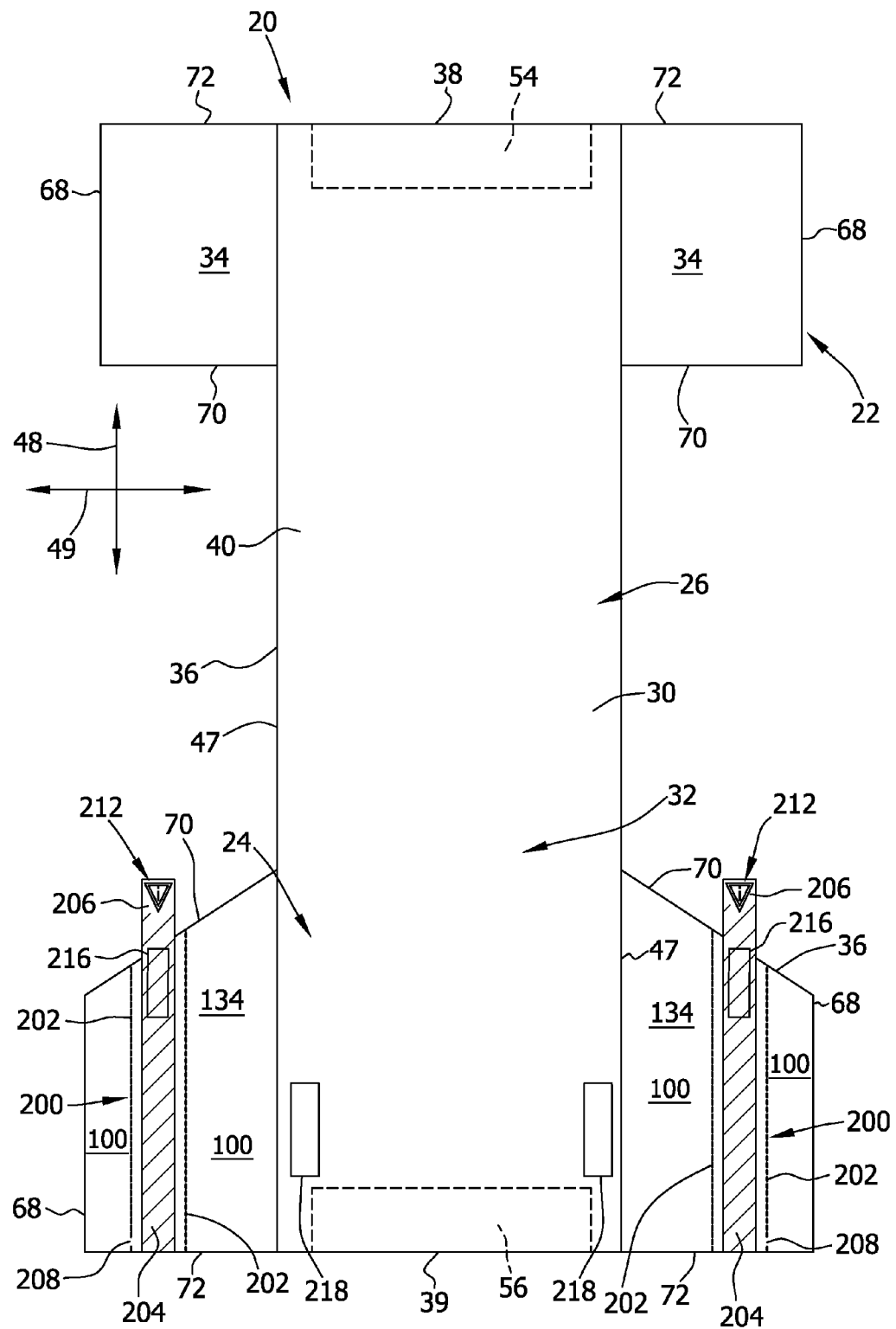
FIG. 2 is a bottom plan view of the training pant of FIG. 1 with the training pant in an unbonded, unfolded and laid flat condition, and showing a surface of the training pant adapted to face away from the wearer during use.
Figure 3:
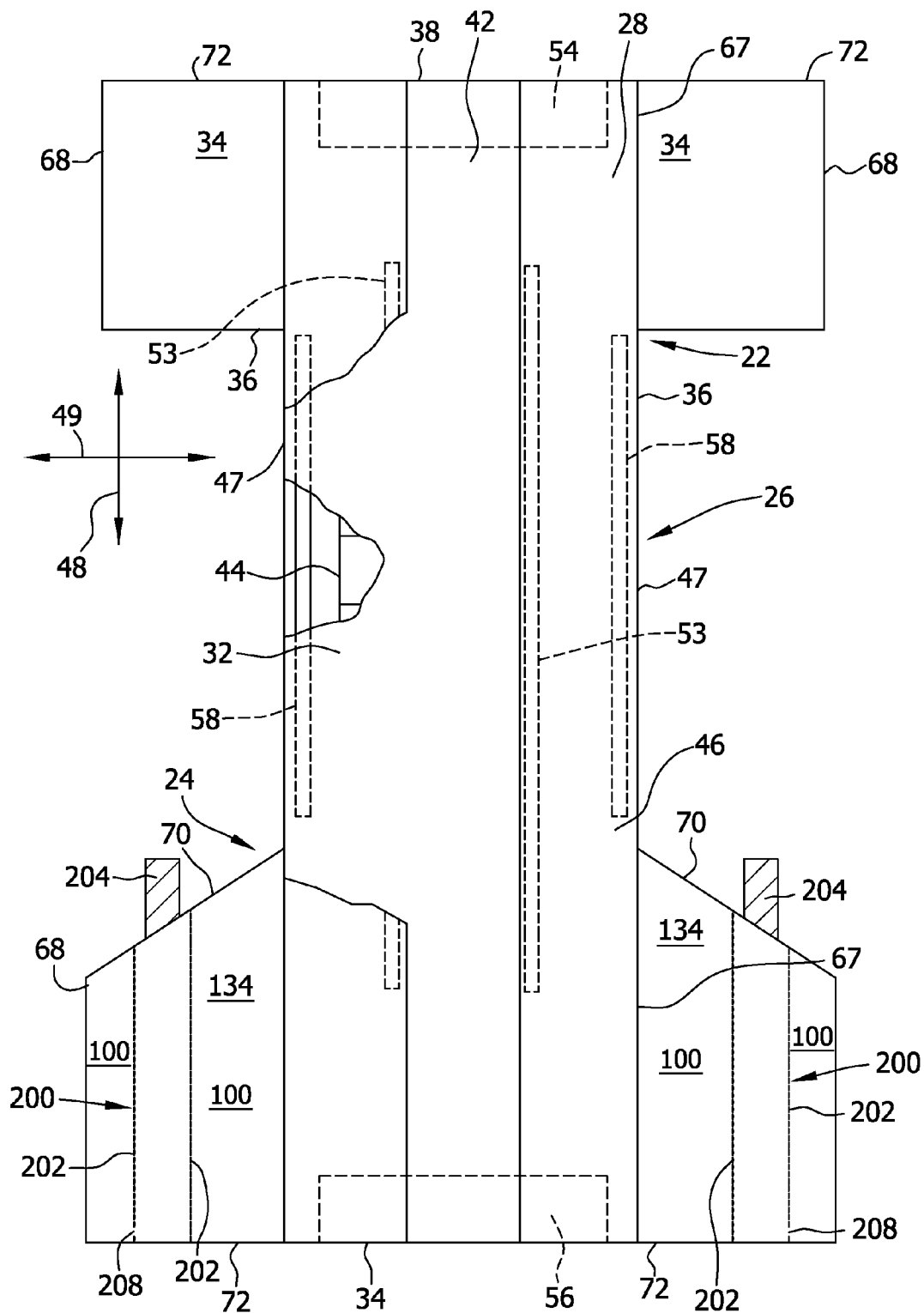
FIG. 3 is a top plan view similar to FIG. 2 but showing a surface of the training pant adapted to face the wearer during use, portions of the training pant being cut away to show underlying features.

With reference to FIG. 2, the training pant 20 includes a central absorbent assembly, generally indicated at 32, which when laid flat as in FIGS. 2 and 3 can be rectangular or any other desired shape. A pair of laterally opposite front side panels 34 extends outward from the absorbent assembly 32 at the front waist region 22 (thereby forming transversely outer portions of the front waist region, and more broadly in part forming transversely opposite sides of the training pant 20). Laterally opposite back side panels 134 extend outward from the absorbent assembly 32 at the back waist region 24 (thereby forming transversely outer portions of the back waist region, and together with the front side panels 34 further defining the sides of the pant 20). Arrows 48 and 49 in FIGS. 2 and 3 depict the orientation of a longitudinal axis and a transverse or lateral axis, respectively, of the training pant 20.

The central absorbent assembly 32 of the illustrated embodiment comprises an outer cover 40 and a bodyside liner 42 connected to the outer cover 40 in a superposed relation by suitable means such as adhesives, ultrasonic bonds, thermal bonds, pressure bonds, or combinations thereof. An absorbent structure 44 (FIG. 3) is disposed between the outer cover 40 and the bodyside liner 42. A pair of containment flaps 46 (FIG. 3) is secured to the bodyside liner 42 for inhibiting the lateral flow of body exudates. Alternatively, the containment flaps 46 may be integrally formed with the bodyside liner 42. The central absorbent assembly 32 has opposite ends which form portions of the front and back waist edges 38 and 39, and opposite side edges 47 which form portions of the side edges 36 of the training pant 20 (FIGS. 2 and 3).

In one suitable embodiment and as seen in FIGS. 1-3, the absorbent assembly 32 and side panels 34, 134 comprise two or more separate elements. In other suitable embodiments, the absorbent assembly 32 and the side panels 34, 134 may be integrally formed with one another. Integrally formed side panels 34, 134 and absorbent assembly 32 would comprise at least some common materials, such as the bodyside liner, flap composite, outer cover, other materials and/or combinations thereof, and could define a one-piece elastic, stretchable, or nonstretchable pant 20.

As illustrated in FIG. 1, the front and back side panels 34, 134 are attached to each other at side seams 66 to define an assembled, or wear, configuration of the pant 20 having a waist opening 50 and a pair of leg openings 52. In the illustrated embodiment, the front and back side panels 34, 134 are non-releasably attached to one another using a suitable attachment method such as, for example, adhesive bonding, ultrasonic bonding, thermal bonding, pressure bonding, or combinations thereof.

With the training pant 20 in the wear configuration, as illustrated in FIG. 1, the front waist region 22 comprises the portion of the training pant 20 which, when worn, is positioned at least in part on the front of the wearer while the back waist region 24 comprises the portion of the training pant 20 which is positioned at least in part on the back of the wearer. The crotch region 26 of the training pant 20 comprises the portion of the training pant 20 which is positioned between the legs of the wearer and covers the lower torso of the wearer.

The front and back side panels 34, 134 comprise the portions of the training pant 20 (and more particularly of the front and back waist regions 22, 24) which, when worn, are positioned on the hips of the wearer. The attached side panels 34, 134 thus broadly define the transversely opposite sides of the pant 20, with each side extending from the waist opening 50 to the respective leg opening 52 at the side seam 66. The waist edges 38, 39 of the training pant 20 are configured to encircle the waist of the wearer and together define the waist opening 50 (FIG. 1). Portions of the side edges 36 in the crotch region 26 generally define the leg openings 52.

The central absorbent assembly 32 is configured to contain and/or absorb exudates discharged from the wearer. The outer cover 40 suitably comprises a material which is substantially liquid impermeable. The outer cover 40 can be a single layer of liquid impermeable material, but more suitably comprises a multi-layered laminate structure in which at least one of the layers is liquid impermeable. For instance, the outer cover 40 can include a liquid permeable outer layer and a liquid impermeable inner layer that are suitably joined together by an adhesive, ultrasonic bonding, thermal bonding, pressure bonding, or combinations thereof. Suitable adhesives can be applied continuously or intermittently as beads, a spray, parallel swirls, or the like. The liquid permeable outer layer can be any suitable material, including materials that provide a generally cloth-like texture. The outer layer may also be made of those materials of which the liquid permeable bodyside liner 42 is made. While it is not a necessity for the outer layer to be liquid permeable, it is suitable that it provides a relatively cloth-like texture to the wearer.

The inner layer of the outer cover 40 can be both liquid and vapor impermeable, or it may be liquid impermeable and vapor permeable. The inner layer can be manufactured from a thin plastic film, although other flexible liquid impermeable materials may also be used. The inner layer, or the liquid impermeable outer cover 40 when a single layer, prevents waste material from wetting articles, such as bed sheets and clothing, as well as the wearer and caregiver.

If the outer cover 40 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 40. One suitable "breathable" material is composed of a microporous polymer film or a nonwoven fabric that has been coated or otherwise treated to impart a desired level of liquid impermeability.

It is also contemplated that the outer cover 40 may be stretchable, and more suitably elastic. In particular, the outer cover 40 is suitably stretchable and more suitably elastic in at least the transverse, or circumferential direction of the pant 20. In other embodiments the outer cover 40 may be stretchable, and more suitably elastic, in both the transverse and the longitudinal direction.

The liquid permeable bodyside liner 42 is illustrated as overlying the outer cover 40 and absorbent structure 44, and may, but need not, have the same dimensions as the outer cover 40. The bodyside liner 42 is suitably compliant, soft feeling, and non-irritating to the wearer's skin. The bodyside liner 42 is also sufficiently liquid permeable to permit liquid body exudates to readily penetrate through its thickness to the absorbent structure 44. Further, the bodyside liner 42 can be less hydrophilic than the absorbent structure 44 to present a relatively dry surface to the wearer and permit liquid to readily penetrate through its thickness. The hydrophilic/hydrophobic properties can be varied across the length, width and/or depth of the bodyside liner 42 and absorbent structure 44 to achieve the desired wetness sensation or leakage performance.

The bodyside liner 42 can be manufactured from a wide selection of web materials, such as porous foams, reticulated foams, apertured plastic films, woven and nonwoven webs, or a combination of any such materials. For example, the bodyside liner 42 may comprise a meltblown web, a spunbonded web, or a bonded-carded-web composed of natural fibers, synthetic fibers or combinations thereof. The bodyside liner 42 may be composed of a substantially hydrophobic material, and the hydrophobic material may optionally be treated with a surfactant or otherwise processed to impart a desired level of wettability and hydrophilicity. The surfactant can be applied by any conventional means, such as spraying, printing, brush coating or the like. The surfactant can be applied to the entire bodyside liner 42 or can be selectively applied to particular sections of the bodyside liner, such as the medial section along the longitudinal center line.

The bodyside liner 42 may also be stretchable, and, more suitably, it may be elastomeric. In particular, the bodyside liner 42 is suitably stretchable and more suitably elastomeric in at least the transverse 49, or circumferential direction of the pant 20. In other embodiments the bodyside liner 42 may be stretchable, and more suitably elastomeric, in both the transverse 49 and the longitudinal 48 directions.

Suitable elastomeric materials for construction of the bodyside liner 42 can include elastic strands, LYCRA elastics, cast or blown elastic films, nonwoven elastic webs, meltblown or spunbond elastomeric fibrous webs, as well as combinations thereof. Examples of suitable elastomeric materials include KRATON elastomers, HYTREL elastomers, ESTANE elastomeric polyurethanes (available from Noveon of Cleveland, Ohio), or PEBAX elastomers. The bodyside liner 42 can also be made from extensible materials as are described in U.S. patent application Ser. No. 09/563,417 filed on May 3, 2000 by Roessler et al. or from biaxially stretchable materials as are described in U.S. patent application Ser. No. 09/698,512 filed on Oct. 27, 2000 by Vukos et al., both of which are hereby incorporated by reference.

The absorbent structure 44 is suitably compressible, conformable, non-irritating to a wearer's skin, and capable of absorbing and retaining liquids and certain body wastes. For example, the absorbent structure 44 may comprise cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents or the like, as well as combinations thereof. In a particular embodiment, the absorbent structure comprises a matrix of cellulosic fluff and superabsorbent hydrogel-forming particles. The cellulosic fluff may include a blend of wood pulp fluff. Suitable types of fluff include, for example, fluff pulp commercially available from Weyerhaeuser Company of Federal Way, Wash., U.S.A. under the designation FR416 (7.5 percent Moisture) and CF416 (7.5 percent Moisture).

The materials may be formed into a web structure by employing various conventional methods and techniques. For example, the absorbent structure 44 may be formed by a dry-forming technique, an air forming technique, a wet-forming technique, a foam-forming technique, or the like, as well as combinations thereof. Furthermore, the absorbent structure 44 may itself encompass multiple layers in a Z-direction (e.g., thickness) of the absorbent structure 44. Such multiple layers may take advantage of differences in absorbent capacity, such as by placing a lower absorbent capacity material layer closer to the bodyside liner 42 and a higher absorbent capacity material closer to the outer cover 40. Likewise, discrete portions of a single-layered absorbent structure may encompass higher capacity absorbents, and other discrete portions of the structure may encompass lower capacity absorbents.

Superabsorbent material is suitably present in the absorbent structure 44 in an amount of from about 0 to about 100 weight percent based on total weight of the absorbent structure 44. The absorbent structure 44 may suitably have a density within the range of about 0.10 to about 0.60 grams per cubic centimeter. Superabsorbent materials are well known in the art and can be selected from natural, synthetic, and modified natural polymers and materials. The superabsorbent materials can be inorganic materials, such as silica gels, or organic compounds, such as crosslinked polymers. Typically, a superabsorbent material is capable of absorbing at least about 10 times its weight in liquid, and preferably is capable of absorbing more than about 25 times its weight in liquid. Suitable superabsorbent materials are readily available from various suppliers. For example, Hysorb T 9700 superabsorbent, which is commercially available from BASF of Ludwigshafen, Germany, or Favor SXM 5600 superabsorbent, which is commercially available from Evonik of Essen, Germany.

The absorbent structure 44 may alternatively comprise a coform material. The term "coform material" generally refers to composite materials comprising a mixture or stabilized matrix of thermoplastic fibers and a second non-thermoplastic material. As an example, coform materials are made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic absorbent materials, treated polymeric staple fibers and the like. Any of a variety of synthetic polymers may be utilized as the melt-spun component of the coform material. For instance, in certain aspects, thermoplastic polymers can be utilized. Some examples of suitable thermoplastics that can be utilized include polyolefins, such as polyethylene, polypropylene, polybutylene and the like; polyamides; and polyesters. In one aspect, the thermoplastic polymer is polypropylene. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al.; which are incorporated herein by reference.

In one suitable embodiment, the absorbent structure 44 is stretchable so as not to inhibit the stretchability of other components to which the absorbent structure may be adhered, such as the outer cover 40 and the bodyside liner 42. After being formed or cut to a desired shape, the absorbent structure 44 may be wrapped or encompassed by a suitable wrap (not shown) that aids in maintaining the integrity and shape of the absorbent structure 44. As best seen in FIG. 3, the absorbent structure 44 of the illustrated embodiment is generally rectangular, although the absorbent structure 44 can have any suitable shape and size.

The central absorbent assembly 32 may also include a surge management layer (not shown) located adjacent the absorbent structure 44 (e.g., between the absorbent structure 44 and the bodyside liner 42) to help decelerate and diffuse surges or gushes of liquid that may be rapidly introduced into the absorbent structure 44 of the training pant 20 by the wearer. Desirably, the surge management layer can rapidly accept and temporarily hold the liquid prior to releasing the liquid into the storage or retention portions of the absorbent structure 44. Examples of suitable surge management layers are described in U.S. Pat. No. 5,486,166 issued Jan. 23, 1996 to Bishop et al.; U.S. Pat. No. 5,490,846 issued Feb. 13, 1996 to Ellis et al.; and U.S. Pat. No. 5,820,973 issued Oct. 13, 1998 to Dodge, II et al., the entire disclosures of which are hereby incorporated by reference.

The central absorbent assembly 32 is configured to contain and/or absorb exudates discharged from the wearer. For example, the containment flaps 46 are configured to provide a barrier to the transverse flow of body exudates. A flap elastic member 53 (FIG. 3) can be operatively joined with each containment flap 46 in any suitable manner. The elasticized containment flaps 46 define a partially unattached edge which assumes an upright configuration in at least the crotch region 26 of the training pant 20 to form a seal against the wearer's body during use. In one suitable embodiment, the containment flaps 46 are located along the side edges 36 of the pant 20, and extend longitudinally along the entire length of the absorbent assembly 32. In other suitable embodiments, the containment flaps 46 only extend partially along the length of the absorbent assembly 32.

To further enhance containment and/or absorption of body exudates, the training pant 20 also suitably includes a front waist elastic member 54, a rear waist elastic member 56, and leg elastic members 58. The waist elastic members 54, 56 can be attached to the outer cover 40 and/or the bodyside liner 42 along the opposite waist edges 38, 39, and can extend over part or all of the waist edges. The leg elastic members 58 can be attached to the outer cover 40 and/or the bodyside liner 42 along the opposite side edges 36 and positioned in the crotch region 26 of the training pant 20. The leg elastic members 58 can be longitudinally aligned along each side edge 47 of the absorbent assembly 32.

The flap elastic members 53, the waist elastic members 54, 56, and the leg elastic members 58 can be formed of any suitable elastic material. Suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic retractive forces are imparted to the substrate. In one suitable embodiment, for example, the flap elastic members 53, the waist elastic members 54, 56, and/or the leg elastic members 58 comprise a plurality of dry-spun coalesced multifilament spandex elastomeric threads sold under the trade name LYCRA® and available from Invista of Wichita, Kans., U.S.A.

Other suitable materials from which the flap elastic members 53, the waist elastic members 54, 56, and the leg elastic members 58 may be constructed include vertical filament laminate (VFL) materials, elastic nonwoven composites having an apertured elastic film laminated to one or more nonwoven web materials, single- and dual-faced spandex laminates, stretch-bonded laminates (SBL), and continuous filament stretch-bonded laminates (CFSBL). A VFL is a composite material having at least one gatherable layer such as a nonwoven material and at least one elastic layer. One type of vertical filament laminate is disclosed, for example, by U.S. Pat. No. 6,916,750 to Thomas et al., which is incorporated herein by reference. Examples of elastic nonwoven composites having an apertured elastic film laminated to one or more nonwoven web materials are described in U.S. Pat. No. 7,803,244 issued Sep. 28, 2010 to Siqueira et al., and U.S. Pat. No. 8,361,913 issued Jan. 29, 2013 to Siqueira et al., both of which are incorporated herein by reference. Examples of single- and dual-faced spandex laminates, SBLs, and CFSBLs are described in U.S. Pat. No. 5,385,775 issued Jan. 31, 1995 to Wright; U.S. Pat. No. 6,057,024 issued May 2, 2000 to Mleziva et al.; and U.S. Pat. No. 6,969,441 issued Nov. 29, 2005 to Welch et al., all of which are incorporated herein by reference.

As noted previously, the illustrated training pant 20 includes front and back side panels 34, 134 defining transversely opposite sides of the pant 20 in the wear configuration. The side panels 34, 134 can be permanently attached along attachment seams 67 to the central absorbent assembly 32 in the respective front and back waist regions 22 and 24. More particularly, the front side panels 34 can be permanently attached to and extend transversely outward beyond the side edges 47 of the absorbent assembly 32 in the front waist region 22, and the back side panels 134 can be permanently attached to and extend transversely outward beyond the side edges 47 of the absorbent assembly 32 in the back waist region 24. The side panels 34, 134 may be attached to the absorbent assembly 32 using suitable attachment means such as, for example, adhesives, ultrasonic bonds, thermal bonds, pressure bonds, or combinations thereof. Alternatively, the side panels 34, 134 can be formed as an integral portion of a component of the absorbent assembly 32. For example, the side panels can comprise a generally wider portion of the outer cover 40, the bodyside liner 42, and/or another component of the absorbent assembly 32.

The front and back side panels 34, 134 each have an outer edge 68 spaced laterally from the attachment seam 67, a leg end edge 70 disposed toward the longitudinal center of the training pant 20, and a waist end edge 72 disposed toward a longitudinal end of the training pant 20. The leg end edge 70 and waist end edge 72 extend from the side edges 47 of the absorbent assembly 32 to the outer edges 68. The leg end edges 70 of the side panels 34, 134 form part of the side edges 36 of the training pant 20. One or more of the leg end edges 70 may be suitably curved and/or angled (such as the leg end edges 70 of the back side panels 134) relative to the transverse axis 49 to provide a better fit around the wearer's legs. The waist end edges 72 are suitably parallel to the transverse axis 49. The waist end edges 72 of the front side panels 34 form part of the front waist edge 38 of the training pant 20, and the waist end edges 72 of the back side panels 134 form part of the back waist edge 39 of the pant 20.

The side panels 34, 134 suitably, although not necessarily, comprise a stretchable material capable of stretching in a direction generally parallel to the transverse axis 49 of the training pant 20. More suitably the side panels 34, 134 comprise an elastic material. Suitable elastic materials, as well as one process of incorporating stretchable side panels into training pants, are described in the following U.S. patents: U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular embodiments, the stretch material may comprise a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; European Patent Application No. EP 0 217 032 published on Apr. 8, 1987 in the name of Taylor et al.; and PCT application WO 01/88245 in the name of Welch et al.; all of which are incorporated herein by reference.

Alternatively, the side panel material may comprise other woven or nonwoven materials, such as the materials described above as being suitable for the outer cover 40 or bodyside liner 42, mechanically pre-strained composites, stretchable but inelastic materials, and combinations thereof. In one suitable alternative embodiment, the side panels 34, 134 comprise a material that is non-stretchable in at least a circumferential direction of the training pant 20.

Referring again to FIG. 1, the training pant 20 includes a tear away section, indicated generally at 200, on each side of the training pant 20. Each tear away section 200 is configured to be physically separated from one or more components of the training pant 20 along a line of weakness 202 (FIGS. 2-4) when a user applies a sufficient amount of force to the tear away section 200. The tear away sections 200 illustrated in FIG. 1 are configured to detach the front waist region 22 of the training pant 20 from the back waist region 24 along the side panels of the training pant 20, and thereby facilitate rapid removal of the training pant 20 as compared to conventional methods of doffing the training pant 20.

As shown in FIGS. 1-4, each tear away section 200 is defined by lines of weakness 202, and includes a reinforcing element 204 and a grip tab 206 to facilitate grasping and applying a tearing force to the tear away section 200.

The lines of weakness 202 separate the tear away sections 200 from adjacent non-tear away sections 100 of the training pant 20, and have a reduced strength as compared to the portions of the training pant 20 adjacent the lines of weakness 202 to provide a relatively low resistance path along which a tear in the training pant 20 can propagate.

The term "line of weakness" as used herein, refers to any region or area of weakened material, preferably having a length, but not necessarily a defined width. A "line of weakness" can include linear and non-linear patterns, such as curvilinear patterns of weakness, or other shapes, such as circles, rectangles, and so forth. A line of weakness can include a perforated line or other series of cuts or openings, a thinning or breakage or separation of material, a weakened line formed by joining two sections of material together (e.g., by pressure bonds), a strip of a different kind of material bridging between adjacent portions of material that is more easily torn or broken than the adjacent portions, and which allows the user or manufacturer to separate the adjacent portions along the line of weakness, or any other suitable configuration or combination of configurations. A line of weakness can further include a single extended slit or cut. In embodiments having a line of weakness formed by perforations or other cuts or openings, it is understood that the spacing between the perforations, cuts, or openings can be increased or decreased to affect a tear-away strength of a tear away section defined by the zones of weakness.

In the illustrated embodiment, the lines of weakness 202 which define the tear away sections 200 are perforated lines formed by mechanically treating the side panels 134 of the training pant 20.

In the illustrated embodiment, each line of weakness 202 includes a non-weakened portion 208 configured to maintain attachment between the tear away section 200 and an adjacent non-tear away section 100 when the tear away section 200 is torn. Maintaining attachment between the tear away section 200 and the training pant 20 reduces the number of discrete pieces that need to be disposed of after use of training pant 20. In the illustrated embodiment, each non-weakened portion 208 is an interruption, or break, in one of the perforated lines.

It is contemplated that the tear away sections 200 can also be completed removed from the training pant 20. In one suitable embodiment, for example, the lines of weakness 202 do not include a non-weakened portion 208 such that the tear away sections 200 may be completely removed from the training pant 20.

In the illustrated embodiment, each tear away section 200 is defined by two lines of weakness 202, although the tear away sections 200 may be defined by any suitable number of lines of weakness that enable the training pant 20 to function as described herein. In one suitable embodiment, for example, at least one tear away section 200 is defined by a single line of weakness, such as a curved or semi-circular line of weakness having both of its ends terminating at the waist opening 50 (see FIG. 7).

The reinforcing element 204 is configured to increase the tear strength of the tear away section 200 to prevent the training pant 20 from tearing along undesired tear lines (e.g., along a tear line perpendicular to the intended tearing direction). More specifically, the reinforcing element 204 is configured to provide the tear away section 200 with a tear strength greater than the force required to separate or tear the tear away section 200 from the training pant 20 (i.e., the threshold force). In one suitable embodiment, for example, each tear away section 200 has a tear strength that is at least about 10% greater than the threshold force of the tear away section 200, at least about 20% greater than the threshold force of the tear away section 200, and even more suitably, at least about 25% greater than the threshold force of the tear away section 200.

The reinforcing element 204 may be constructed from a variety of suitable materials, including spunbonded webs, meltblown webs, spunbond-meltblown-spunbond (SMS) webs, and combinations thereof. The reinforcing element 204 may also be constructed from synthetic polymer fibers, including polyolefins (e.g., polyethylene, polypropylene, polybutylene), polyamides, polyesters, and combinations thereof. In one suitable embodiment, the reinforcing element 204 is formed by a bond connecting one of the front side panels 34 to a respective back side panel 134 along one of the side seams 66, such as an adhesive bond, an ultrasonic bond, a thermal bond, a pressure bond, or combinations thereof.

In the illustrated embodiment, the reinforcing element 204 is formed from a separate piece of material and attached to the training pant 20. The reinforcing element 204 may be attached to the training pant 20 using any suitable attachment method such as, for example, adhesive bonding, ultrasonic bonding, thermal bonding, pressure bonding, or combinations thereof. In other suitable embodiments, the reinforcing element 204 may be integrally formed with the tear away section 200.

The reinforcing element 204 of each tear away section 200 is positioned adjacent the lines of weakness 202, and extends along the entirety of each line of weakness 202. In the illustrated embodiment, each tear away section 200 includes one reinforcing element 204, although it is contemplated that the tear away sections 200 may include more than one reinforcing element. In one suitable embodiment, for example, a tear away section includes two reinforcing elements spaced apart from one another and positioned adjacent a respective line of weakness.

The grip tab 206 is attached to the tear away section 200, and is sized and positioned to facilitate grasping and pulling the tear away section 200 to separate the tear away section 200 from the training pant 20 along the lines of weakness 202. In the illustrated embodiment, the grip tab 206 is attached to the reinforcing element 204, although in other suitable embodiments the grip tab 206 may be attached to any other suitable portion of the tear away section 200 that enables the training pant 20 to function as described herein. Further, in the illustrated embodiment, the grip tab 206 is positioned proximate an end of the tear away section 200, and extends beyond a leg end edge 70 of the training pant 20.

The grip tab 206 has a suitable width 210 to enable a user to readily grasp the tear away section 200 by the grip tab 206. In one suitable embodiment, for example, the grip tab has a width 210 of between about 2 millimeters (mm) and about 10 mm, more suitably between about 3 mm and about 5 mm, and, even more suitably, between about 4 mm and about 5 mm.

In the illustrated embodiment, the grip tab 206 is positioned at the bottom of the tear away section 200 proximate a respective leg opening 52, and projects beyond a respective leg end edge 70 of the training pant 20. In other suitable embodiments, the grip tab 206 may be positioned at the top of the tear away section 200 proximate the waist opening 50, and project beyond a respective waist edge 38, 39 of the training pant 20. In yet other suitable embodiments, the grip tab 206 may be substantially flush with an edge of the training pant 20 (e.g., one of the leg end edges 70 or a waist edge 38, 39), or may be recessed from an edge of the training pant 20. In embodiments in which the grip tab 206 is substantially flush with or recessed from an edge of the training pant 20, the edges of the training pant 20 may include notches positioned on each side of the grip tab 206 to facilitate grasping the grip tab 206.

In the illustrated embodiment, the grip tab 206 also includes a visual cue 212 to enhance the noticeability of the grip tab 206 and the tear away section 200, and thereby provide sufficient visual awareness to a user of the presence the grip tab 206 and the tear away section 200. The visual cue 212 may include any suitable cue that enhances the noticeability of the grip tab 206 and/or the tear away section 200 including, for example, graphics, colors, texturing, and combinations thereof. In the illustrated embodiment, the visual cue 212 comprises a printed graphic located on the outer surface 30 of the training pant 20. In other suitable embodiments, the tear away section 200 may include additional and/or other visual cues located on portions of the tear away section 200 other than the grip tab 206 to enhance the noticeability of the tear away section 200.

The grip tab 206 may be constructed from a variety of suitable materials, including nonwoven materials such as SMS webs, spunbonded webs, meltblown webs, polyolefin-based nonwovens, and combinations thereof. The grip tab 206 may be suitably textured or tactilely different from other components of the tear away section 200 to facilitate grasping the grip tab 206. Additionally or alternatively, the grip tab 206 may be constructed from a rubber-like material, such as spandex-based elastomerics, to provide a relatively tacky surface for grasping the grip tab 206.

In the illustrated embodiment, the grip tab 206 is formed integrally with the reinforcing element 204 and, more specifically, is an extension of the reinforcing element 204. In other suitable embodiments, the grip tab 206 is formed as a discrete component and is attached to the tear away section 200 using any suitable attachment method such as, for example, adhesive bonding, ultrasonic bonding, thermal bonding, pressure bonding, or combinations thereof.

The tear away sections 200 may be located at any suitable location on the training pant 20, including, for example, the front waist region 22, the back waist region 24, the crotch region 26, the side panels 34, 134, and the absorbent assembly 32. In the illustrated embodiment, the tear away sections 200 are located on side panels of the training pant 20, specifically the back side panels 134. As noted above, however, the tear away sections 200 may be located at any suitable location on the training pant 20 that enables the training pant 20 to function as described herein. In one suitable embodiment, for example, the tear away sections 200 are located on the front side panels 34. In another suitable embodiment, the tear away sections 200 are located on both the front side panels 34 and the back side panels 134. In yet another suitable embodiment, a tear away section 200 may be located on the absorbent assembly 32 (e.g., within the front waist region 22 of the training pant 20).

The tear away sections 200 may have any suitable size, shape, and orientation that enables the training pant 20 to function as described herein. In the illustrated embodiment, each tear away section 200 has a generally rectangular shape, and extends substantially parallel to the longitudinal direction 48 of the training pant 20 from the back waist edge 39 to a respective leg end edge 70. As shown in FIG. 1, when the training pant 20 is in the wear configuration, each tear away section 200 extends from the waist opening 50 to a respective leg opening 52. In other suitable embodiments, the tear away section 200 may be angled with respect to the longitudinal direction 48 of the training pant 20, and extend towards the front waist region 22 or the back waist region 24.

Figure 4:
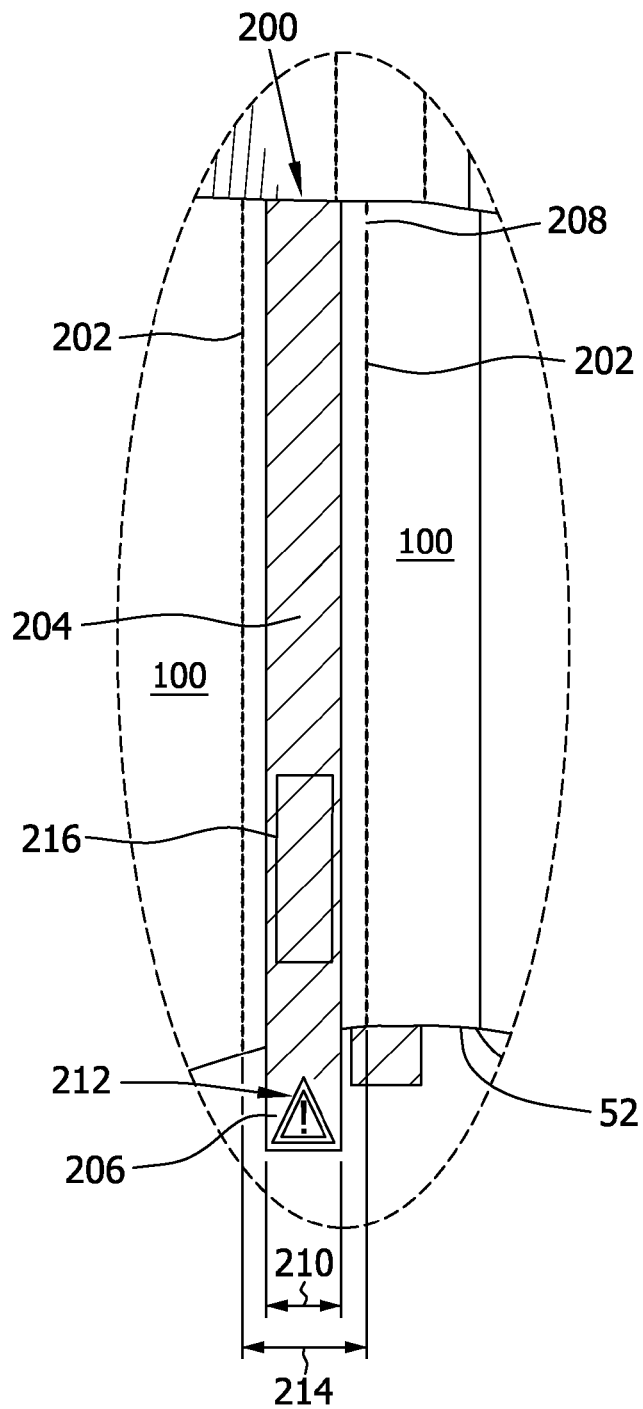
FIG. 4 is an enlarged side perspective view of the tear away section of the training pant of FIG. 1.

As shown in FIG. 4, the tear away section 200 has a width 214 taken along a direction perpendicular to the intended tear direction of the tear away section 200. The width 214 of the tear away section 200 may be greater than, less than, or substantially equal to the width 210 of the grip tab 206. In the illustrated embodiment, the width of the tear away section 200 is substantially equal to the width 210 of the grip tab 206. In one suitable embodiment, the width 214 of the tear away section 200 is between about 3 mm and 15 mm, more suitably between about 5 mm and about 7 mm, and even more suitably, the width 214 of the tear away section 200 is about 6 mm.

The training pant 20 may also include a disposal fastening system to facilitate securing the training pant 20 in a compact disposal configuration after the tear away sections 200 are separated from the training pant 20. In the illustrated embodiment, for example, the training pant includes a first fastening component 216 disposed on the tear away section 200, and a second fastening component 218 disposed on the outer cover 40. The first and second fastening components 216, 218 are configured to matingly engage one another to secure the training pant 20 in a compact disposal configuration to facilitate disposal of the training pant 20. The first fastening component 216 and the second fastening component 218 may include any suitable fasteners that enable the training pant 20 to function as described herein, including, for example, complementary hook and loop fasteners, other complementary mechanical fasteners, adhesive fasteners, cohesive fasteners, and combinations thereof.

Figure 5:
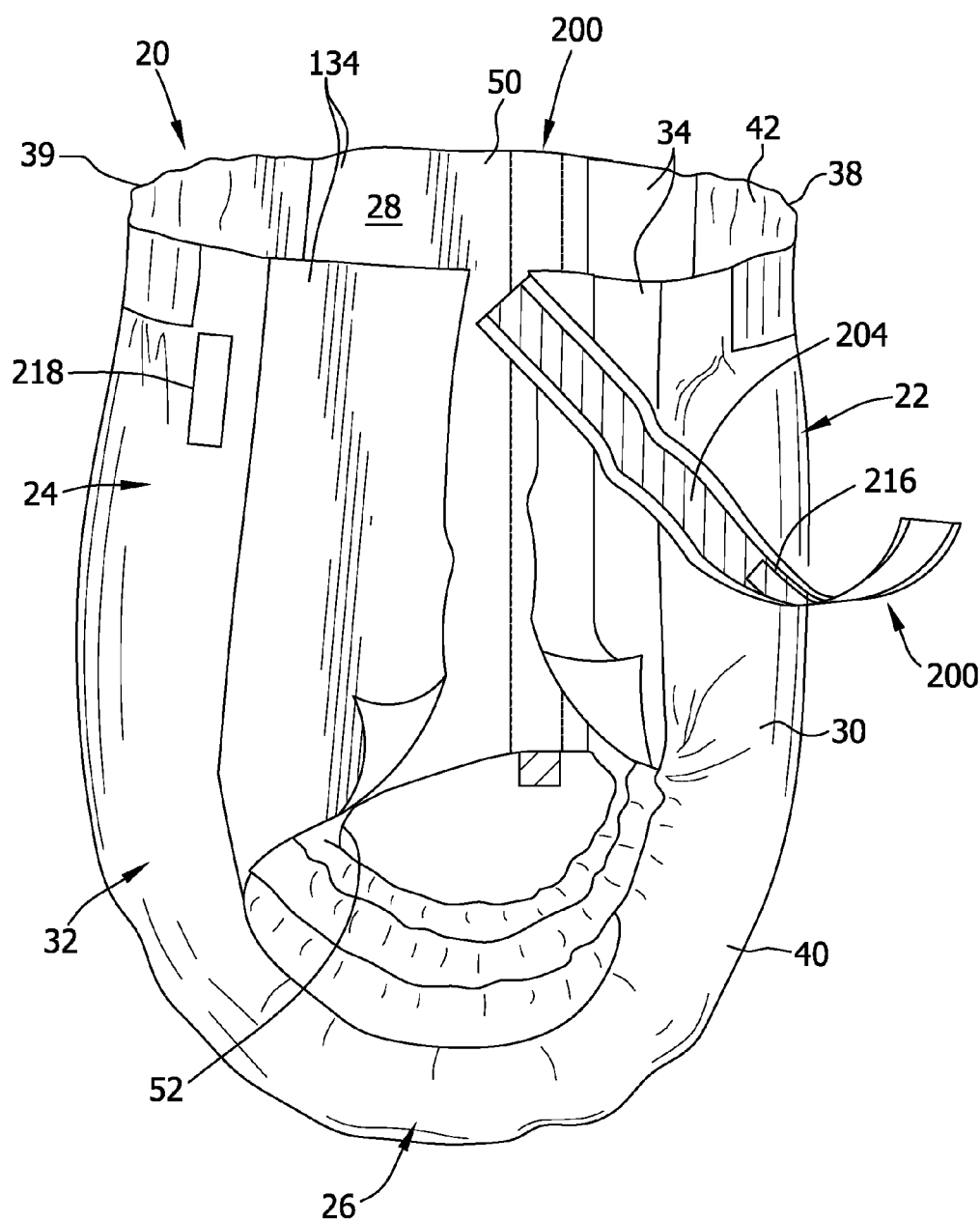
FIG. 5 is a side perspective of the training pant of FIG. 1 with the tear away section torn along lines of weakness to separate the front waist region from the back waist region.

As described herein, each tear away section 200 of the illustrated embodiment is configured to be separated from the training pant 20 when a sufficient amount of force (i.e., a threshold force) is applied thereto. Tearing, or activating, the tear away sections 200 transforms the training pant 20 from a closed, wear configuration (shown in FIG. 1), to an open configuration (partially illustrated in FIG. 5) such that the training pant 20 can be easily removed as compared to conventional methods of doffing the training pant 20.

Suitably, the threshold force for activating the tear away sections 200 is between about 200 grams-force (gf) and about 2000 gf, more suitably, between about 400 gf and about 1500 gf, and even more suitably, between about 300 gf and about 1000 gf. Further, the tear away sections 200 are configured to inhibit activation during ordinary wear of the training pant 20, while having a relatively low threshold force so that the tear away sections 200 are easy for the user to tear.

In one suitable method of tearing away the tear away sections 200, the user grasps one tear away section 200 with one hand, and the other tear away section 200 with the other hand. The user suitably grasps each tear away section 200 by a respective grip tab 206. The user then pulls the tear away sections 200 upwards towards the waist opening 50, causing the lines of weakness 202 to begin tearing or separating the tear away section 200 from the adjacent non-tear away sections 100. It is contemplated that the tear away sections 200 may be pulled in a direction other than towards the waist opening 50 to activate the tear away sections 200, such as towards a respective leg opening 52.

The user continues to pull the tear away sections 200 upwards towards the waist opening 50 causing at least one line of weakness 202 of each tear away section 200 to be completely torn from a respective leg opening 52 to the waist opening 50, thereby separating the tear away section 200 from an adjacent non-tear away section, and transforming the training pant into its opened configuration. With the training pant 20 in its opened configuration (partially illustrated in FIG. 5), the training pant 20 can be easily removed from the wearer, as compared to conventional methods of doffing the training pant.

As described above, the illustrated tear away sections 200 can be separated from the training 20 with a single hand. The illustrated tear away sections thereby facilitate relatively quick and easy removal from the wearer, as compared to known absorbent articles which require two hands to separate a single side seam.

Figure 6:
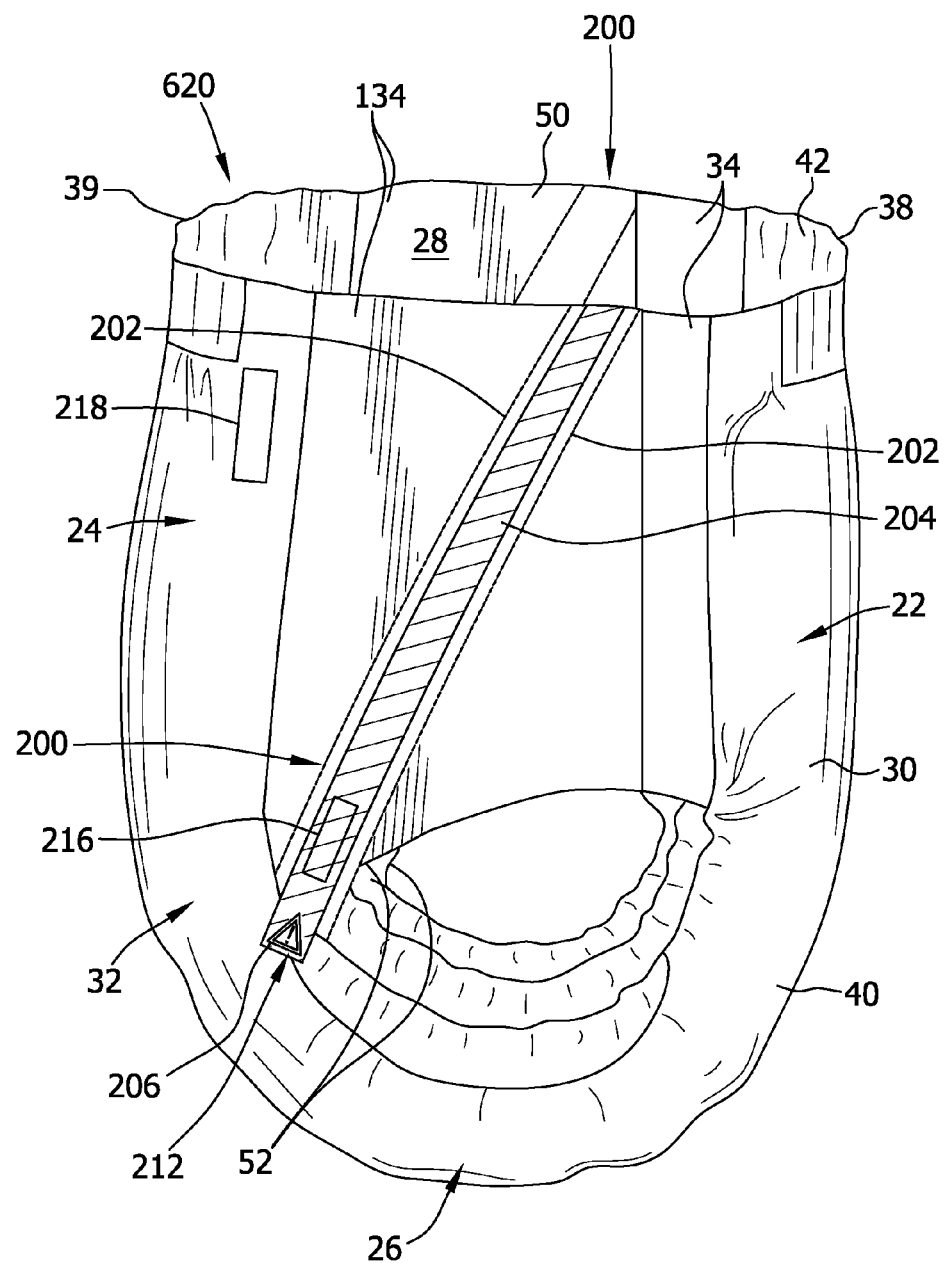
FIG. 6 is a side perspective of another suitable embodiment of an absorbent article, also shown in the form of a training pant, including a tear away section.

FIG. 6 illustrates an alternative embodiment of an absorbent article, also in the form of a training pant 620, including tear away sections 200 extending from a respective leg opening 52 towards the front waist region 22 to the waist opening 50. The orientation of the tear away sections 200 shown in FIG. 6 provides the wearer of the article with an ergonomic path of motion along which the tear away sections 200 can be torn. Moreover, the grip tabs 206 are positioned proximate a respective leg opening 52 of the training pant 620, and are thus readily accessible to the wearer of the training pant 620. The configuration and orientation of the tear away sections 200 shown in FIG. 6 are particularly suitable for articles intended to be removed by the wearer of the article while being worn, such as incontinence articles.

Figure 7:
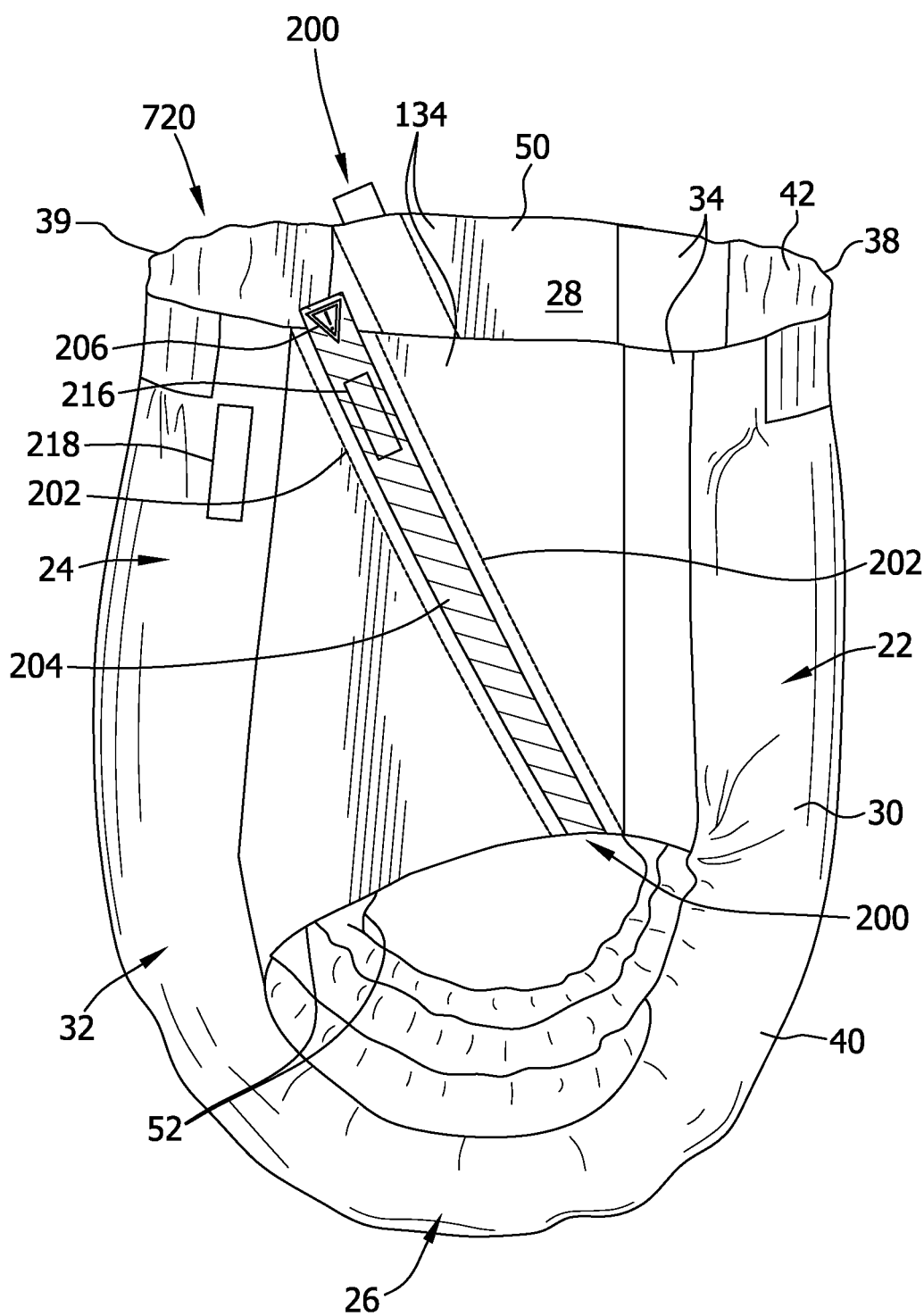
FIG. 7 is a side perspective of a yet another suitable embodiment of an absorbent article, also shown in the form of a training pant, including a tear away section.

FIG. 7 illustrates another alternative embodiment of an absorbent article, also in the form of a training pant 720, including tear away sections 200 extending from a respective leg opening 52 towards the back waist region 24 to the waist opening 50. The orientation of the tear away sections 200 shown in FIG. 7 makes removal of the training pant 720 by the wearer difficult, particularly when the grip tab 206 is positioned proximate the waist opening 50 of the training pant 720, as shown in FIG. 7. Such a configuration is particularly suitable for articles intended to be removed by a user other than the wearer of the absorbent article, such as diapers and training pants.

Figure 8:
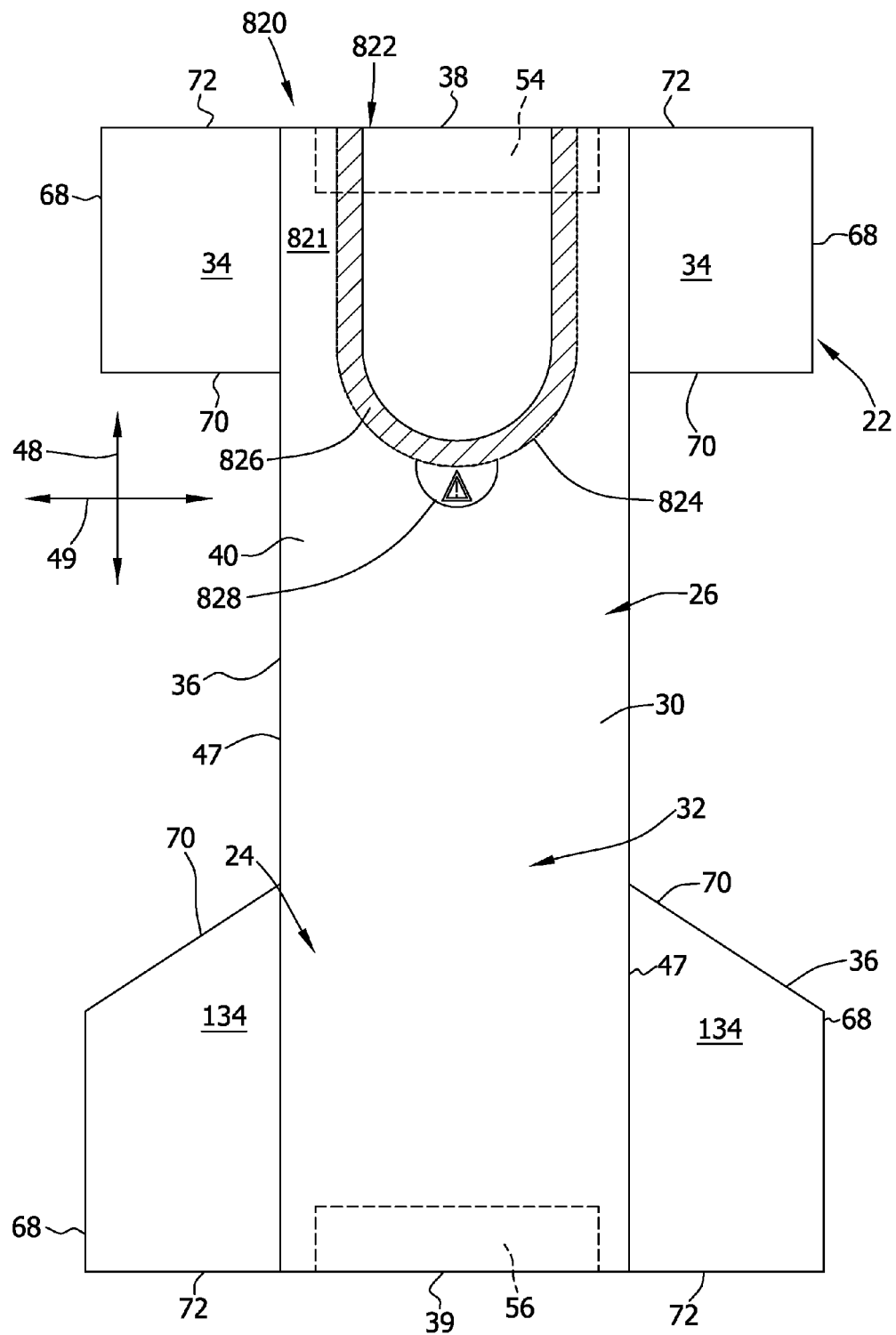
FIG. 8 is a bottom plan view of still another suitable embodiment of an absorbent article, also shown in the form of a training pant, including a tear away section on the front waist region of the training pant.

FIG. 8 illustrates another alternative embodiment of an absorbent article, also in the form of a training pant 820, including a tear away section 822 located on the central absorbent assembly 32 within the front waist region 22 of the training pant 820. When torn, the tear away section 822 illustrated in FIG. 8 provides an access opening for the wearer of the training pant 820 through which bodily fluids may be discharged.

In the embodiment illustrated in FIG. 8, the tear away section 822 is defined by a single, continuous line of weakness 824, and includes a reinforcing element 826 and a grip tab 828. Further, in the embodiment illustrated in FIG. 8, the tear away section 822 includes a portion of the outer cover 40, a portion of the bodyside liner 42, and a portion of the front waist elastic member 54.

The line of weakness 824 separates the tear away section 822 from an adjacent non-tear away section 821 of the training pant 820, and has a reduced strength as compared to the portions of the training pant 820 adjacent the line of weakness 824 to provide a relatively low resistance path along which a tear in the training pant 820 can propagate. In the embodiment illustrated in FIG. 8, the line of weakness 824 is a perforated line, although any suitable line of weakness may be utilized in the training pant 820, such as the lines of weakness described herein with reference to FIGS. 1-4. Further, in the embodiment illustrated in FIG. 8, the line of weakness 824 includes two ends that terminate at the front waist edge 38.

The reinforcing element 826 is configured to increase the tear strength of the tear away section 822 to prevent the training pant 820 from tearing along undesired tear lines (e.g., along a tear line perpendicular to the intended tearing direction). The reinforcing element 826 provides the tear away section 822 with a tear strength greater than the threshold force needed to separate the tear away section 822 from the training pant 820.

The reinforcing element 826 may be constructed from substantially the same materials as those described herein with reference to the reinforcing element 204 shown in FIGS. 1-4. Further, the reinforcing element 826 may be formed as a separate piece of material and attached to the training pant 820.

In the embodiment illustrated in FIG. 8, the reinforcing element 826 is positioned adjacent the line of weakness 824, and extends along the entirety of the line of weakness 824.

The grip tab 828 is attached to the tear away section 822, and is sized and positioned to facilitate grasping and pulling the tear away section 822 to separate the tear away section 822 from the training pant 820 along the line of weakness 824. In the illustrated embodiment, the grip tab 828 is attached to the reinforcing element 826, although in other suitable embodiments the grip tab 828 may be attached to any other suitable portion of the tear away section 822 that enables the training pant 720 to function as described herein. For example, in one suitable embodiment, the grip tab 828 is attached to the portion of the outer cover 40 within the tear away section 822, such as at the front waist edge 38.

The grip tab 828 may be constructed from substantially the same materials as those described herein with reference to the grip tab 206 shown in FIGS. 1-4. Further, the grip tab 828 may be formed as a separate piece of material and attached to the tear away section 822, as shown in FIG. 8, or the grip tab 828 may be integrally formed with one or more components of the tear away section 822 such as, for example, the reinforcing element 826.

In the embodiment illustrated in FIG. 8, the tear away section 822 extends from the front waist edge 38 towards the back waist region 24. In the embodiment illustrated in FIG. 8, the tear away section 822 extends from the front waist edge 38 into the crotch region 26 of the training pant 820, although it is contemplated that the tear away section 822 may extend into the back waist region 24. It is further contemplated that the tear away section 822 may extend only into the front waist region 22.

Further, as noted above, the tear away section 822 includes a portion of an elastic member, specifically the front waist elastic member 54. More specifically, the line of weakness 824 overlaps the front waist elastic member 54. Other suitable embodiments may include tear away sections with lines of weakness that overlap other waist elastic members, such as the rear waist elastic member 56 or the leg elastic members 58. In one suitable embodiment, for example, the waist elastic members 54, 56 extend into the front and back side panels 34, 134, respectively, and the training pant includes tear away sections positioned on one of the front and back side panels 34, 134. In embodiments having a tear away section that includes a portion of an elastic member, the elastic member may be rendered less elastic or inelastic (i.e., "deadened"), within the tear away section.

The following examples are provided for purposes of illustration only.

EXAMPLES

Eight samples were tested for activation force (or threshold force) and tear strength, as described below. Each sample was constructed by adhesively bonding a strip of spunbond-meltblown-spunbond (SMS) nonwoven material to an elastic nonwoven material commercially available from Kimberly-Clark Professional of Roswell, Ga. under the product designation NWRE-00694.

Test Methods

Tear Strength Test

The tear strength of each sample was measured to determine the peak force required to tear the tear away section under tensile loading.

Each test sample was prepared by adhesively bonding a strip of SMS nonwoven material having a width of about 7 mm to an elastic nonwoven material commercially available from Kimberly-Clark Professional of Roswell, Ga. under the product designation NWRE-00694 using 0.1 grams of a hot-melt adhesive commercially available from Bostik Findley (formerly known as Ato Findley) of Wauwatosa, Wis. under the product designation H-2525-A. The strip of SMS nonwoven material had a basis weight of 57.8 gsm, and included a 15.3 gsm polypropylene meltblown layer sandwiched between two, 21.25 gsm, polypropylene spunbond outer layers. The component layers of the SMS nonwoven material were bonded together with sufficient strength to withstand the testing without delamination or tearing. Each test sample was then cut to a width of 25.4 mm and a length of 152.4±3 mm.

The test sample was then loaded into an MTS Type 500S tensile tester or equivalent commercially available from MTS Systems Corporation. More specifically, the test sample was clamped between a stationary grip and a moving grip in the tensile tester such that the lengthwise direction of the sample was aligned parallel to the direction of testing and force application.

Once the test sample was loaded in the tensile tester, the test sample was loaded according the following parameters:

| | |
|---|---|
| Crosshead Speed | 508 mm/minute ± 10 mm/minute (20 ± 0.4 inch/minute) |
| Gage Length | 25.4 mm |
| Load Units | Grams-force |
| Start Calculation | 16 mm |
| End Calculation | 225 mm |

The tear strength of the test sample (i.e., the peak load measured during the test) was recorded to the nearest 0.1 grams-force.

Operation of the tensile tester and data acquisition were carried out using MTS TestWorks® for Windows, commercially available from MTS Systems Corporation. The tear strength tests were carried out in a controlled testing environment having a temperature of 23±2° C. (73.4±3.6° F.) and a relative humidity of 50±5%.

Activation Force (or Threshold Force) Test

The activation force (or threshold force) was measured to determine the peak force required to separate a tear away section from an absorbent article.

Each test sample was prepared by adhesively bonding a strip of SMS nonwoven material having a width of about 7 mm to an elastic nonwoven material commercially available from Kimberly-Clark Professional of Roswell, Ga. under the product designation NWRE-00694 using 0.1 grams of a hot-melt adhesive commercially available from Bostik Findley (formerly known as Ato Findley) of Wauwatosa, Wis. under the product designation H-2525-A. The strip of SMS nonwoven material had a basis weight of 57.8 gsm, and included a 15.3 gsm polypropylene meltblown layer sandwiched between two, 21.25 gsm, polypropylene spunbond outer layers. The component layers of the SMS nonwoven material were bonded together with sufficient strength to withstand the testing without delamination or tearing.

The test sample was then cut to a width of 25.4 mm and a length of 152.4±3 mm. Lines of weakness extending along the length of the test sample were formed on each side of the strip of SMS nonwoven material. The lines of weakness were formed by perforations having a length of 3 mm and being spaced apart in the lengthwise direction by 2 mm of the elastic nonwoven material.

The test sample was then loaded into an MTS Type 500S tensile tester or equivalent commercially available from MTS Systems Corporation. More specifically, the test sample was clamped between a stationary grip and a moving grip in the tensile tester such that the lengthwise direction of the sample was aligned parallel to the direction of testing and force application. The portion of the test sample between the lines of weakness was placed in the moving grip, and the portion of the test sample outside of the lines of weakness was placed in the stationary grip.

Once the test sample was loaded in the tensile tester, the test sample was loaded according the following parameters:

| | |
|---|---|
| Crosshead Speed | 508 mm/minute ± 10 mm/minute (20 ± 0.4 inch/minute) |
| Gage Length | 25.4 mm |
| Load Units | Grams-force |
| Start Calculation | 16 mm |
| End Calculation | 225 mm |

The threshold force needed to separate the tear away section from adjacent non-tear away sections (i.e., the peak load measured during the test) was recorded to the nearest 0.1 grams-force.

Test Results

The test results of the tear strength tests and the activation force (or threshold force) tests are provided below in Tables I and II, respectively.

TABLE I

Results of Tear Strength Testing

| Test Sample No. | Tear Strength (gf) |
|---|---|
| 1 | 594.2 |
| 2 | 602.7 |
| 3 | 1000.6 |
| 4 | 484.1 |
| 5 | 785.7 |
| 6 | 1113.8 |
| 7 | 307.7 |
| 8 | 1365.8 |

TABLE II

Results of Activation Force (Threshold Force) Testing

| Test Sample No. | Perforation Size (mm)/ Spacing (mm) | Threshold Force (gf) |
|---|---|---|
| 1 | 3/2 | 349.9 |
| 2 | 3/2 | 442.5 |
| 3 | 3/2 | 326.4 |
| 4 | 3/2 | 394.8 |
| 5 | 3/2 | 835.7 |
| 6 | 3/2 | 756.6 |
| 7 | 3/2 | 675.2 |
| 8 | 3/2 | 723.0 |

With reference to Table I, the tested samples ranged from a minimum tear strength of 307.7 gf to a maximum tear strength of 1365.8 gf. The average tear strength of the tested samples was about 781.8 gf. With reference to Table II, the tested samples ranged from a minimum threshold force of 349.9 gf to a maximum threshold force of about 835.7 gf. The average threshold force of the tested samples was about 563.0 gf.

To this end, in one suitable embodiment each tear away section 200 has a tear strength that is at least about 10% greater than the threshold force of the tear away section 200, at least about 20% greater than the threshold force of the tear away section 200, and even more suitably, at least about 25% greater than the threshold force of the tear away section 200. In another suitable embodiment, the threshold force for activating the tear away sections 200 is between about 200 gf and about 2000 gf, more suitably, between about 400 gf and about 1500 gf, and even more suitably, between about 300 gf and about 1000 gf. The threshold force for activating the tear away sections 200 may be increased as compared to the values provided herein, for example, by decreasing the size of the perforations used to form the lines of weakness and/or by increasing the spacing between the perforations. The threshold force for activating the tear away sections 200 may be decreased as compared to the values provided herein, for example, by increasing the size of the perforations used to form the lines of weakness and/or by decreasing the spacing between the perforations.

When introducing elements of the present invention or the preferred embodiment(s) thereof, the articles "a", "an", "the", and "said" are intended to mean that there are one or more of the elements. The terms "comprising," "including", and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A disposable absorbent article having transversely opposite sides, the article comprising:
   a bodyside liner;
   an outer cover;
   an absorbent body disposed between the liner and the outer cover;
   a front waist region, a back waist region and a crotch region extending between and interconnecting the front and back waist regions, the front and back waist regions being attached to each other by side panels at least partially defining leg openings and a waist opening of the absorbent article, the side panels attaching the front and back waist regions together at side seams; and
   a tear away section disposed on one of the sides of the article and at least in part traversing the respective side seam, the tear away section being configured to be torn from the absorbent article when at least a threshold force is applied to the tear away section, the tear away section extending from the waist opening to a respective leg opening and being defined by lines of weakness, only one of the lines of weakness including a non-weakened portion, the tear away section having a tear strength greater than the threshold force, wherein the non-weakened portion is configured to attach the tear away section and the absorbent article when the threshold force is applied to the tear away section.

2. The absorbent article as set forth in claim 1, wherein the tear strength of the tear away section is at least 10% greater than the threshold force.

3. The absorbent article as set forth in claim 1, wherein the tear strength of the tear away section is at least 25% greater than the threshold force.

4. The absorbent article as set forth in claim 1, wherein the tear away section is disposed along one of the side panels.

5. The absorbent article as set forth in claim 1, wherein the tear away section is defined by two lines of weakness, each line of weakness extending from the waist opening to the respective leg opening.

6. The absorbent article as set forth in claim 1, wherein the tear away section extends from the respective leg opening towards the front waist region to the waist opening.

7. The absorbent article as set forth in claim 1, wherein the tear away section extends from the respective leg opening towards the back waist region to the waist opening.

8. The absorbent article as set forth in claim 1, wherein the tear away section has a width between about 3 mm to about 15 mm.

9. The absorbent article as set forth in claim 1, wherein the side panels are non-stretchable in a circumferential direction of the absorbent article.

10. The absorbent article as set forth in claim 1, wherein the threshold force is between about 200 grams-force and about 2000 grams-force.

11. The absorbent article as set forth in claim 1, wherein the threshold force is between about 300 grams-force and about 1000 grams-force.

12. The absorbent article as set forth in claim 1, wherein the tear strength of the tear away section is between about 300 grams-force and about 1400 grams-force.

13. The absorbent article as set forth in claim 1, wherein a reinforcing element is positioned adjacent at least one of the lines of weakness.

14. The absorbent article as set forth in claim 13, wherein the reinforcing element is defined by a bond attaching the side panels.

15. The absorbent article as set forth in claim 1, wherein the tear away section extends from the respective leg opening towards the front waist region to the waist opening, and a grip tab is positioned at a bottom of the tear away section proximate the respective leg opening.

16. The absorbent article as set forth in claim 1, wherein the tear away section extends from the respective leg opening towards the back waist region to the waist opening, and a grip tab is positioned at a top of the tear away section proximate the waist opening of the absorbent article.

* * * * *